(12) United States Patent
Yen et al.

(10) Patent No.: US 7,718,775 B2
(45) Date of Patent: May 18, 2010

(54) MONOCLONAL ANTIBODY WITH THE CAPABILITY OF NEUTRALIZING ENTEROVIRUS TYPE 71 INFECTION

(75) Inventors: Jui-Hung Yen, Tainan (TW);
Hung-Jung Wang, Tai-Ping (TW);
Huan Yao Lei, Tainan (TW);
Chun-Keung Yu, Tainan (TW);
Ya-Fang Wang, Tainan (TW)

(73) Assignee: ScinoPharm Taiwan, Ltd., Tainan County (TW)

( * ) Notice: Subject to any disclaimer, the term of this patent is extended or adjusted under 35 U.S.C. 154(b) by 147 days.

(21) Appl. No.: 11/403,070

(22) Filed: Apr. 12, 2006

(65) Prior Publication Data

US 2006/0292693 A1    Dec. 28, 2006

Related U.S. Application Data

(60) Provisional application No. 60/671,229, filed on Apr. 14, 2005.

(51) Int. Cl.
*C07K 16/00* (2006.01)
*C07K 16/08* (2006.01)

(52) U.S. Cl. .............. 530/387.3; 530/387.1; 530/388.1; 530/388.3

(58) Field of Classification Search ........................ None
See application file for complete search history.

(56) References Cited

U.S. PATENT DOCUMENTS 5,230,888 A * 7/1993 Baltimore et al. ........ 424/186.1

6,150,508 A * 11/2000 Murphy et al. ........... 530/387.1

OTHER PUBLICATIONS

GenPept AAA61594, anti-fluorescein antibody, (Jan. 1995).*
GenPept AAT73715, immunoglobulin gamma heavy chain variable region [Mus musculus] (Oct. 2004).*
Hawkins et al.,"Adapting antibodies for clinical use," BMJ vol. 305 No. 6865, pp. 1348-1352 (Nov. 1992).*
Hovi et al., "Peptide antisera targeted to a conserved sequence in poliovirus capsid VP1 cross-react widely with members of the genus Enterovirus," Journal of Clincal Microbiology, vol. 31 No. 5, pp. 1083-1087 (May 1993).*
Hsueh et al., "Acute encephalomyelitis during an outbreak of enterovirus type 71 infection in Taiwan: report of an autopsy case with pathologic, immunofluorescence, and molecular studies," Modern Pathology, vol. 13 No. 11, pp. 1200-1205 (Nov. 2000).*
Rudikoff et al., "Single Amino Acid Substitution Altering Antigen-Binding Specificity," Proceedings of the National Academy of Sciences, USA, vol. 79 No. 6, pp. 1979-1983 (Mar. 1982).*
Vihinien-Ranta et al., "The VP1 N-terminal sequence of canine parvovirus affects nuclear transport of capsids and efficient cell infection," Journal of Virology, vol. 76 No. 4, pp. 1884-1891 (Feb. 2002).*
Wu et al., "Protection against lethal enterovirus 71 infection in newborn mice by passive immunization with subunit VP1 vaccines and inactivated virus," Vaccine, vol. 20 No. 5-6, pp. 895-904 (Dec. 2001).*

(Continued)

*Primary Examiner*—Zachariah Lucas
(74) *Attorney, Agent, or Firm*—Cohen Pontani Lieberman & Pavane LLP

(57) ABSTRACT

The present invention provides a monoclonal antibody capable of neutralizing EV71 infection.

5 Claims, 6 Drawing Sheets

OTHER PUBLICATIONS

GenPept S45249, "Ig heavy chain precursor V region (Mab 1G3)—mouse (fragment)," Jan. 2000.*

Sassano et al., "PCR amplification of antibody variable regions using primers that anneal to constant regions," Nucleic Acids Research, vol. 22 No. 9, pp. 1768-1769 (May 1994).*

* cited by examiner

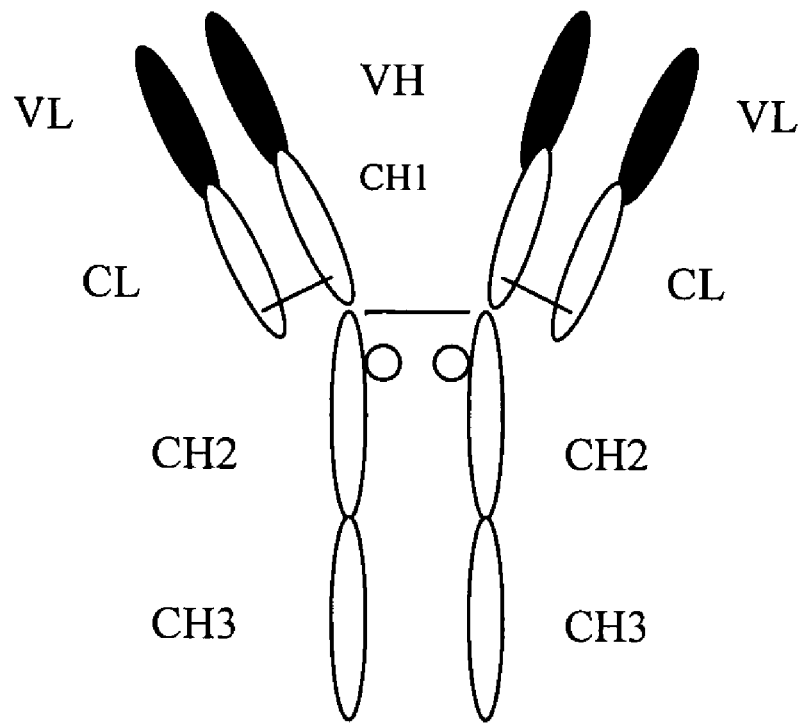
Fig. 1
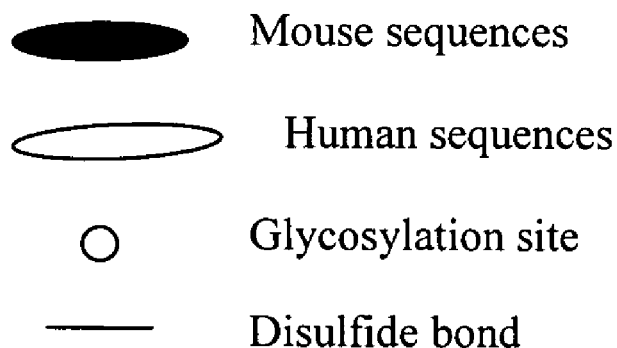
V: variable region
C: constant region
H: heavy chain
L: light chain

V_H:

atgaaggtgtggttaaactggctacttcctttattctgtcggtaacttcagggtctac
M  K  V  W  L  N  W  L  L  P  F  I  L  S  V  T  S  G  V  Y
tcagaggttcagctccagcagtctgggactgtgctggcaaggcctggggcttcagtgaag
S  E  V  Q  L  Q  Q  S  G  T  V  L  A  R  P  G  A  S  V  K
atgtcctgcaaggcctctggttacaccttaccacctactggatgcactggataaaacag
M  S  C  K  A  S  G  Y  T  F  T  <u>T  Y  W  M  H</u>  W  I  K  Q
aggcctggacagggtctggaatggattggactattttcctggaaatagtgatactagt
R  P  G  Q  G  L  E  W  I  G  <u>T  I  F  P  G  N  S  D  T  S
tacaaccagaagtccaagggcaaggccaaactgactgcagtcacatccaccagcactgcc
Y  N  Q  K  S  K</u>  G  K  A  K  L  T  A  V  T  S  T  S  T  A
tacatggagctcagcagcctgacaaatgaggactctgcggtctactactgtacaagattg
Y  M  E  L  S  S  L  T  N  E  D  S  A  V  Y  Y  C  T  R  <u>L
agggagggctactggggccacggcaccactctcacagtctcctca
R  E  G  Y</u>  W  G  H  G  T  T  L  T  V  S  S

V_L:

atggtatccgcagctcagttccttggtctcctgttgctctgttttcaaggtaccagatgt
M  V  S  A  A  Q  F  L  G  L  L  L  L  C  F  Q  G  T  R  C
gatatccaaatgacacagcctacatcctccctgtctgcctctctgggagacagagtcacc
D  I  Q  M  T  Q  P  T  S  S  L  S  A  S  L  G  D  R  V  T
atcagttgcaggacaagtcaggacattagcaattatttaaactggtatcagcagaaacca
I  S  C  <u>R  T  S  Q  D  I  S  N  Y  L  N</u>  W  Y  Q  Q  K  P
gatggaactgttaaactcctgatctactacaacatcaaaattacactccggagtcccatca
D  G  T  V  K  L  L  I  Y  <u>Y  T  S  K  L  H  S</u>  G  V  P  S
aggttcagtggcagtgggtctggaacagattattctctcaccattgacaacctggaacaa
R  F  S  G  S  G  S  G  T  D  Y  S  L  T  I  D  N  L  E  Q
gaggattttgccacttactttgccaacagggtgacacgcttccgtacacgttcggaggg
E  D  F  A  T  Y  F  C  <u>Q  Q  G  D  T  L  P  Y  T</u>  F  G  G
gggaccaagctggaaataaaacgg
G  T  K  L  E  I  K  R

Fig. 2

(a)
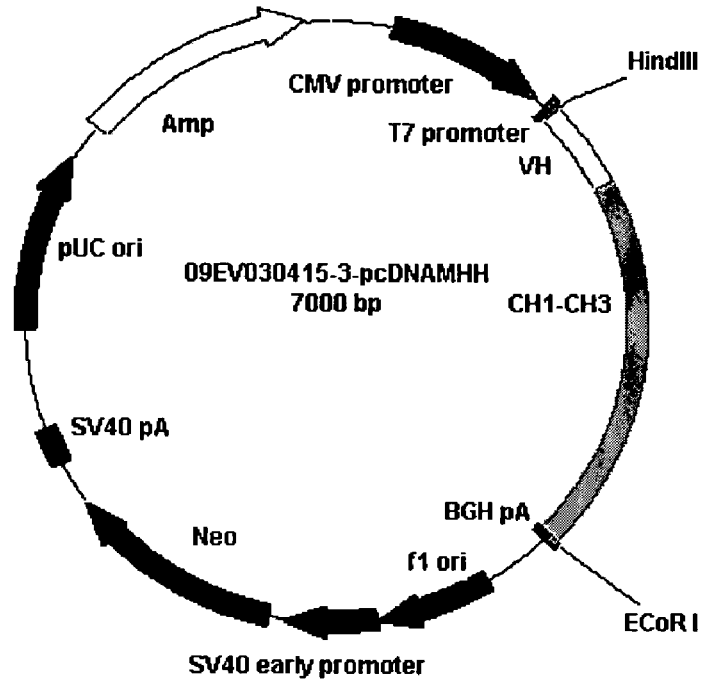
(b)
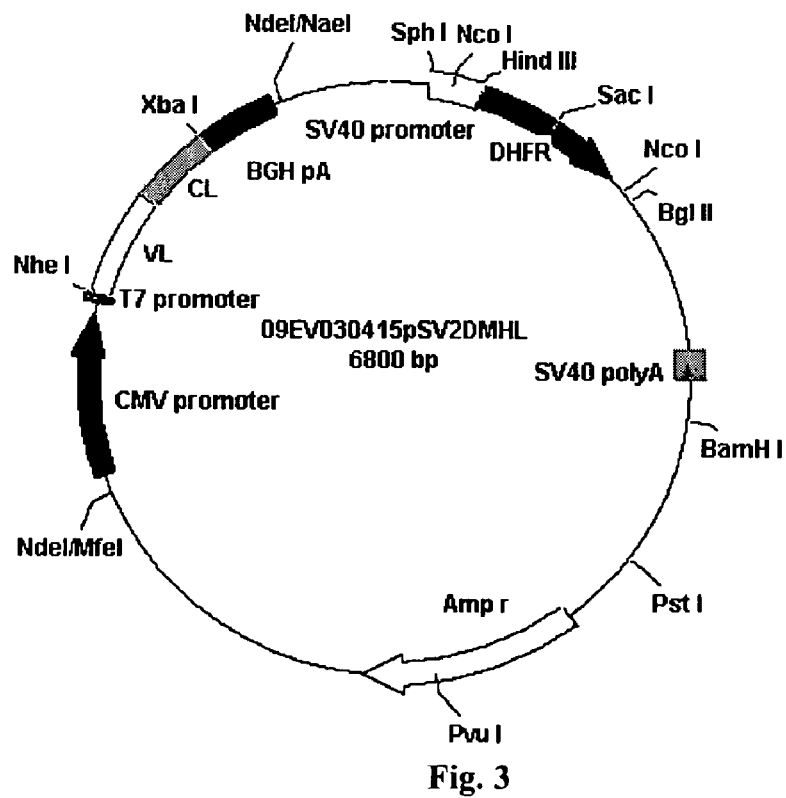
Fig. 3

(a)
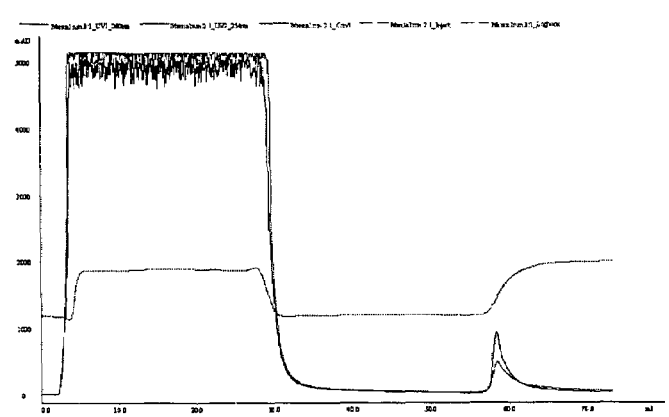
(b)
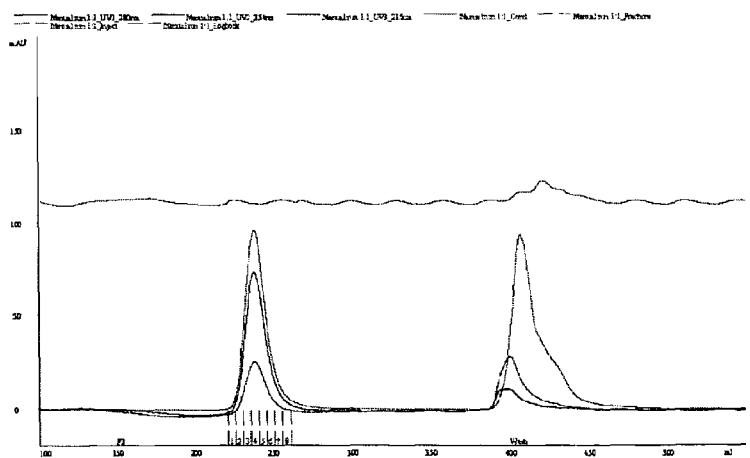
Fig. 5

US 7,718,775 B2

MONOCLONAL ANTIBODY WITH THE CAPABILITY OF NEUTRALIZING ENTEROVIRUS TYPE 71 INFECTION

RELATED APPLICATIONS

This application claims priority from U.S. Provisional Patent Application Ser. No. 60/671,229 which was filed on Apr. 14, 2005, incorporated herein by reference in its entirety.

BACKGROUND OF THE INVENTION

1. Field of the Invention

The present invention relates to a monoclonal antibody with the capability of neutralizing *enterovirus* type 71 infection.

2. Description of the Related Art

Therapeutic monoclonal antibody (mAb) provides a useful and specific tool for curing various infectious diseases and even for some cancers. Using these magic bullets for human, however, those mAbs derived directly from rodent hybridoma may cause severe allergy or immunoresponses. To attenuate or reduce the potential immunogenicity for the therapeutic purposes in human body, each domain of the mAb, except for the variable regions (Fv) which contain CDRs (complementarity determining regions), should be replaced by human counterparts (i.e. constant regions of heavy and light chains). This replacement process is termed humanization or recombination of mAb (see e.g., Boulianne, G. L., et al. (1984) Production of a functional chimeric mouse/human antibody, Nature 312,643-646, incorporated herein as reference by its entirety.)

To humanize a rodent's mAb, variable and constant regions of both heavy and light chains have to be cloned firstly from mouse and human, respectively. Thanks to the advance in molecular cloning technologies, variable regions could be cloned directly by reverse transcription polymerase chain reaction (RT-PCR) from rodent hybridoma using a set of degenerate PCR primers which could amplify DNA fragments between secretory signal sequences and V-J-C junctions. Similar strategy was also used to clone the constant regions of human (see e.g., Morrison, S. L. et al. (1984) Chimeric human antibody molecules; mouse antigen-binding domains with human constant region domains, Proc. Natl. Acad. Sci. USA 81,6841-6855, incorporated herein as reference by its entirety.) FIG. 1 schematically illustrates structures of chimeric monoclonal antibody.

*Enterovirus* 71 (EV71) belongs to the human *Enterovirus* A species of the *Enterovious gneus* within the Piconaviridae family. Since it was discovered in California in 1969 and its infection case was first reported in 1974 in United States, EV71 infection has been reported in at least 12 small and large outbreaks throughout the world, including Taiwan.

In 1998, the largest EV71 epidemic reported to date outbreaked in Taiwan (Ho M. et al. (2000) An Epidemic of *enterovirus* 71 infection in Taiwan. N Engl J Med 341, 929-935), 129,106 cases were reported by sentinel physicians, followed by two smaller epidemics in 2000 and 2001, respectively. Like other types of enteroviral infection, EV71 infection may be asymptomatic or may cause diarrhea, rashes, vesicular lesions on the hands, feet, and oral mucosa (hand-foot-and-mouth disease, HFMD) in young children. Although most of HFMD disease caused by EV71 infection is usually considered a benign disease without central nervous system (CNS) disorders, outbreaks in the Asia-Pacific region, including Japan and Taiwan, appeared with frequent involvements of severe and mortal CNS syndromes such as aseptic meningitis, brainstem encephalitis, acute flaccid paralysis and neurogenic pulmonary oedema.

Since no effective antiviral treatment for severe EV71 infections and no vaccine is available, the only current means to prevent EV71 infection is through avoidance of contact between infected and susceptible individuals.

Accordingly, a monoclonal antibody specific for neutralizing EV71 infection may be an ideal prophylactic treatment for preventing the various debilitating effects or syndromes of the infection by EV71 (Wu C. N. et al. (2001) Protection against lethal enterovirus 71 infection in newborn mice by passive immunization with subunit VP1 vaccines and inactivated virus. Vaccine 20, 895-904.).

SUMMARY OF THE INVENTION

The present invention provides a monoclonal antibody capable of neutralizing EV71 infection. The antibody preferably comprises a constant region and a variable region. The constant region is a human constant region. The variable region, or at least a CDR of the antibody, is derived from a non-human species (e.g., mouse).

In general, the monoclonal antibody retains the binding specificity of a non-human monoclonal antibody and exhibit improved interactions with human effector cells. This results in an improved antibody-dependent cellular cytotoxicity which is presumed to be one of the ways of eliminating the infection by EV71. This antibody binds to EV71 viral particles, including VP1, a major viral surface glycoprotein of EV71.

The antibody in accordance with the present invention is useful in the passive immunization against exposure to EV71. It maybe also useful in related immunotherapies for HFMD.

The monoclonal antibody of the present invention may be a humanized (e.g., either fully or a chimeric) monoclonal antibody, of any species origin, such as murine, ovine, bovine, porcine or avian. Methods of producing antibody molecules with various combinations of "humanized" antibodies are well known in the art and include combining murine variable regions with human constant regions (Cabily, et al. Proc. Natl. Acad. Sci. USA, 81:3273, 1984), or by grafting the murine-antibody complementary determining regions (CDRs) onto the human framework (Richmann, et al., Nature 332:323, 1988) Other general references which teach methods for creating humanized antibodies include Morrison, et al., Science, 229:1202,1985; Jones, et al., Nature, 321:522, 1986; Monroe, et al., Nature 312:779, 1985; Oi, et al., BioTechniques, 4:214, 1986; European Patent Application No. 302,620; and U.S. Pat. No. 5,024,834. Therefore, by humanizing the monoclonal antibodies of the invention for in vivo use, an immune response to the antibodies would be greatly reduced.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

In the drawings:

FIG. 1 is an illustration of the chimeric monoclonal antibody structure.

FIG. 2 shows DNA and deduced amino acid sequences for the monoclonal antibody 1G3 variable region, heavy chain VH (upper)(SEQ ID NOS:1 and 2) and light chain VL(lower) (SEQ ID NOS:3 and 4) domains.

FIG. 3 is a schematic representation of the expression vector used for expressing anti-EV71 chimeric Ab heavy chain and light chain, specifically, FIG. 3(a) relates to the plasmid 09EV030415-3-pcDNAMHH, and FIG. 3(b) relates to the plasmid 09EV030415pSV2DMHL.

FIG. 5 illustrate two-step chromatography for purification of recombinant anti-EV71 chimeric antibody, specifically, FIG. 5(a) shows the profile of sample elution by rProteinA Sepharose column, and FIG. 5(b) shows the profile of product elution by gel filtration column.

DETAILED DESCRIPTION OF THE PRESENTLY PREFERRED EMBODIMENTS

Figure 4:
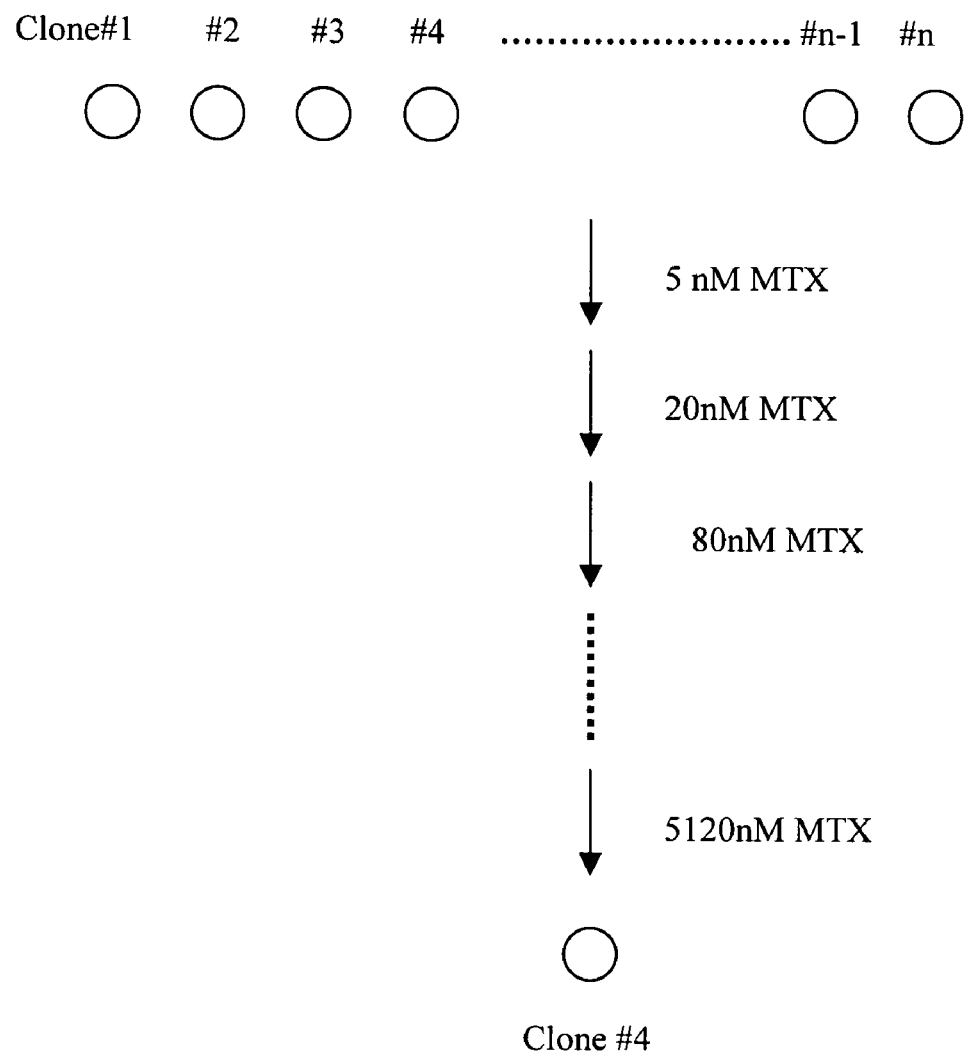
FIG. 4 is schematic amplification of the cell clones for producing the anti-EV71 chimeric monoclonal antibody.

Additional aspects and details of the invention will be apparent from the following examples, which are intended to be illustrative rather than limiting. Example 1 describes the cloning of the heavy chain variable regions from hybridoma cell line 1G3. Example 2 describes the cloning of light chain variable region from hybridoma cell line 1G3. Example 3 describes the cloning of the human heavy chain constant region. Example 4 describes the cloning of the human light chain constant region. Example 5 describes the construction of the expression plasmid for producing the heavy chain and light chain of chimeric monoclonal antibody. Example 6 describes the expression plasmid transfection and cell clone selection. Example 7 describes the amplification of stable transfectants. Example 8 describes the expression and purification of chimeric monoclonal antibody of EV71. Example 9 studies the antigen binding ability of the chimeric antibody in vitro. Example 10 studies the neutralizing activity of the purified chimeric antibody in vitro.

EXAMPLE 1

Example 1 describes the cloning of the heavy chain variable regions from hybridoma cell line 1G3 by using reverse transcriptase-polymerase chain reaction (RT-PCR) method (see, e.g., Coloma, M. J., Larrick, J. W. and Morrison S. L. (1992) Novel vector for the expression of antibody molecules using variable regions generated by polymerase chain reaction. J. Immunol. Methods 152, 89-104, incorporated herein as reference in its entirety.)

Hybridoma Cell Line:

Mouse hybridoma cell line 1G3, obtained from Dr. Chun-Keung Yu (Department of Microbiology & Immunology, College of Medicine, National Cheng-Kung University), producing a neutralizing anti-EV71 immunoglobulin G (IgG) was used in this experiment. The hybridoma cells were grown in Dulbecco's Modified Eagle medium (DMEM, GIBCO) with 10% fetal bovine serum (FBS) supplemented with 4 mM glutanmine (Sigma), 2 g/L sodium bicarbonate, and 10 ug/l pincillin 100 ug/l streptomycine (GIBCO).

Cell Line:

Chinese Hamster Ovary dihydrofolate reductase deficient cells line (CHO-dhfr$^{31}$, ATCC CRL-9096) was purchased from Food Industry Research and Development Institute (HsinChu, Taiwan). The cells were grown in Iscove's Modified Dulbecco's medium (IMDM, GIBCO) supplemented with 4 mM L-glutamine, 1.5 g/L sodium bicarbonate, 0.1 mM hypoxanthine, 0.016 mM thymidine, and 10% FBS. All cells (CHO-dhfr⁻ and hybridoma 1G3) were grown in a humidity-saturated 5% CO2 incubator at 37° C.

Extraction of Hybridoma Cells RNA:

Total RNA from $1.0 \times 10^6$ of hybridoma 1G3 cells was extracted by an RNA purification kit (RNEASY MINI KIT™ (QIAGEN, Cat#74104) according to manufacture's instructions. The purified RNA dissolved in DEPC-treated water (~1-2 μg/μl) was stored at −70° C. for future applications.

Redundant Primers Design:

To obtain the DNA sequences of the variable regions of any antibody (IgG) by using PCR, a set of degenerated primers corresponding to the 5' signal peptide and a 3' constant region (J or CH1 regions) were used (Larrick J. M. et al. (1989) Rapid cloning of rearranged immunoglobulin genes from human hybridoma cells using mixed primers and polymerase chain reaction. Biochemical And Biophysical Research Communications 160, 1250-1256.). The oligonucleotide primers were designed based on the Kabat's database. The design of degenerated primers for each amino acid were included 25 mouse adult, embryo, myeloma, cDNA clones, and hybridoma available sequences. Oigonucleotide primers were provided by ScinoPharm Biotech Oligonucleotide Lab. Detailed information on the redundant primers is provided in the next section: polymerase chain reaction. Table 1 lists the redundant primers for cDNA synthesis and amplification of antibody sequences.

TABLE 1

The redundant primers for amplification of the variable region of 1G3 heavy chain sequence.

a. pLCdT (for first strand cDNA synthesis):
   5'-GCCGGAATTCTAGAAGCTTTTTTTTTTTTTTTTT-3'
   (SEQ ID NO: 5)

b. pHCH1:
   5'-AGGTCTAGAAYCTCCACACACAGGRRCCAGTGGATAGAC-3'
   (SEQ ID NO: 6)

c. pHALT1:
   5'-GGGGATATCCACCATGGRATGSAGCTGKGTMATSCTCTT-3'
   (SEQ ID NO: 7)

d. pHALT2:
   5'-GGGGATATCCACCATGRACTTCGGGYTGAGCTKGGTTTT-3'
   (SEQ ID NO: 8)

e. pHALT3:
   5'-GGGGATATCCACCATGGCTGTCTTGGGGCTGCTCTTCT-3'
   (SEQ ID NO: 9)

Nomenclature: M = AC  R = AG  W = AT  S = CG  Y = CT  K = GT  V = ACG  H = ACT  D = AGT  B = CGT  X = AGCT First-strand cDNA synthesis was performed using a reverse transcription kit (QIAGEN OMNISCRIPT RT KIT™ (Cat#205110) according to manufacture's instructions. Briefly, total RNA samples (~0.5 ug) was preheated at 65° C. for 5 min and incubated with a mixture of RNase inhibitors, deoxynucleotides, oligo (dT)15, or specifically, pLCdT as primer, and Omniscript reverse transcriptase (included in the kit), for 60 min at 42° C.

Polymerase Chain Reaction (PCR):

To clone the variable regions for sequence analysis, PCR primers were designed to hybridize to the leader sequence (5' or forward primer) and to the constant region immediately downstream of the V-J region (3' or reverse primer). All primers had a restriction sites (EcoR V was used for 5' primer; Xba I was used for 3' primer) permitting the cloning of the PCR product into either the subcloning vector (commercial T-A vector, such as pGEM-T from Promega) or the final expression vector (pcDNA3.1(+), Invitrogen). An equimolar amount of each primer was used in the PCR reaction.

PCR reactions were performed in a volume of 100 ul using 2 to 5 ul of cDNA (from first strain cDNA synthesis cocktail), 2 U of Taq polymerase, 200 uM each dNTP, 1 uM of each primer, and 10 ul of 10× Taq polymerase reaction buffer. PCR was carried out for 36 to 40 cycles in a thermal controller (Stratagene, RoboCycler 96) with 1 min denaturing (94° C.), 1 min annealing (55° C.), 2 min extension (72° C.), and a final extension of 10 min. The size of the PCR products was verified by 2% TAE agarose gel stained with ethidium bromide. The correct size was approximately 400 base pair for the heavy chain variable region.

Construction of pTHV1 Vector for DNA Sequencing:

The PCR product was directly cloned into pGEM-T vector, then microliter of the ligation was used for electronic transformation (electroporation) into E. coli DH5 α competent cells. Electroporation of E. coli was performed on an electroporation apparatus (the apparatus GENE PULSER II™ (Bio-Rad) with the conditions of resistance 200 ohms and high voltages 2,500 V applied on a 0.2-cm electrode gap cuvette. Transformants with inserts were picked, miniprep plasmid DNA analyzed and the apparently correct clones sequenced (Mission Biotech Ltd, Taipei, Taiwan). The exact plasmid is named pTHV1. The DNA sequence of variable region was compared and verified by submitting them to an immunoglobulin database IgBLAST). The DNA sequence of heavy chain variable region is a novel antibody sequence and shown in FIG. 2 (VH). The sequences were interpreted according to the Database IgBLSAT. Underlined amino acids comprise the CDRs.

EXAMPLE 2

Example 2 describes the cloning of light chain variable region from hybridoma cell line 1G.

Plasmid 09EV030318-3-pyVk-F:

The plasmid, 09EV030318-3-pyVk-F, containing the variable region cDNA of light chain was produced from hybridoma cells RNA by a reverse transcription and polymerase chain reaction system (ACCESS RT PCR SYSTEM™ (Promega, Cat#A1250) according to the manufacture's instruction. The primers used for RT and PCR were primer mixture containing Mulgk VL5'-F1, Mulgk VL5'-F2, Mulgk VL5'-F3, Mulgk VL5'-F4 and MuCk For primer. The primer sequence is shown in Table 2. The RT reaction was performed at 48° C. for 45 min and the PCR was continuously carried out in the same tube for 40 cycles with 30 sec denaturing (94° C.), 1 min annealing (60° C.), 2 min extension (68° C.), and a final extension of 7 min. The size of the PCR products was verified by 1% TAE agarose gel stained with ethidium bromide. The PCR product (~380 bp) was purified from the agarose gel and cloned into the TA vector (pyT&A vector, Yeaatern), then transferred to E. coli host (DH5α) for plasmid maintaining and DNA sequencing analysis (Mission Biotech Ltd, Taipei, Taiwan). The DNA sequence of variable region was compared and verified by submitting them to an immunoglobulin database IgBLAST. The variable region cDNA sequence of light chain is a novel antibody sequence and shown in FIG. 2(VL). Underlined amino acids comprise the three CDRs.

TABLE 2

The primers for cloning of the light chain variable region of 1G3

| | |
|---|---|
| Mulgk VL5'-F1 | ACTAGTCGACATGAKGTHCYCXGCTCAGYTYCTXRG |
| Mulgk VL5'-F2 | ACTAGTCGACATGGTRTCCWCASCTCAGTTCCTTG |
| Mulgk VL5'-F3 | ACTAGTCGACATGTATATATGTTTGTTGTCTATTTCT |
| Mulgk VL5'-F4 | ACTAGTCGACATGAAGTTGCCTGTTAGGCTGTTGGTGCT |
| MuCk For | CTCATTCCTGTTGAAGCTCTTGAC |

EXAMPLE 3

Example 3 describes the cloning of the human heavy chain constant region.

Plasmid 09EV030303-5-pTHclgG1:

The cDNA of human IgG1 heavy chain was produced from human PBMC total cellular RNA by the Access RT-PCR System kit (Promega) according to manufacture's instruction. The specific primers used for RT and PCR were HUIgGC3-5':5'-ctggcaccctcctccaagagcacctctgggggc-3' (SEQ ID NO:15) and HUIgGC2-3':5'-ggtctagatcatttacccg-gagacaggg-3'(SEQ ID NO:16). The RT reaction was performed at 48° C. for 45 min and the PCR was continuously carried out in the same tube for 40 cycles with 30 sec denaturing (94° C.), 1 min annealing (60° C.), 2 min extension (68° C.), and a final extension of 7 min. The PCR product was analyzed by 1% agarose gel electrophoresis. The cDNA (~1 Kb) was cloned into TA vector and verified by DNA sequencing analysis.

EXAMPLE 4

Example 4 describes the cloning of the human light chain constant region.

Plasmid 09EV030115-pcDNACk8:

The cDNA of human kappa light chain was synthesized by oligonucleotides-based gene synthesis method. Based on the complete coding sequence of kappa light chain (GenBank#AF113887), ten oligonucleotides (Table 3) were produced by ScinoPharm Biotech Oligo Lab for synthesis of the cDNA by PCR method. Briefly, PCR reaction was performed in a volume of 50 ul using 200 ng of each oligonucleotide, 5 U of HiFi proof-reading DNA polymerase (Yeastern), 200 uM each dNTP, and 10 ul of 10× PCR polymerase reaction buffer. PCR was carried out for 30 cycles in a thermal controller (Stratagene, RoboCycler 96) with 50 sec denaturing (95° C.), 50 sec annealing (50° C.), 1 min extension (72° C.), and a final extension of 10 min. The size of the PCR products was verified by 2% TAE agarose gel stained with ethidium bromide. The correct sizes were approximately 320 base pairs for the light chain constant region. The cDNA was digested with ECoR V and Xba I, then cloned into the EcoR V-Xba I site of pcDNA3.1 (+) vector for DNA sequencing analysis.

TABLE 3

The oligonucleotides for synthesis of human kappa light chain cDNA

| | |
|---|---|
| Ck5'-1 | actgtggctgcaccatctgtcttcatcttcccgccatctgat gagcagttgaaat (SEQ ID NO: 17) |
| Ck5'-3 | gctgaataacttctatcccagagaggccaaagtacagtggaa ggtggataacgcc (SEQ ID NO: 18) |
| Ck5'-5 | tcccaggagagtgtcacagagcaggacagcaaggacagcacc tacagcctcagca (SEQ ID NO: 19) |
| Ck5'-7 | ctacgagaaacacaaagtctacgcctgcgaagtcacccatca gggcctgagctcg (SEQ ID NO: 20) |
| Ck3'-2 | tagaagttattcagcaggcacacaacagaggcagttccagat ttcaactgctcat (SEQ ID NO: 21) |
| Ck3'-4 | tctgtgacactctcctgggagttacccgattggagggcgtta tccacctt (SEQ ID NO: 22) |
| Ck3'-6 | ttgtgtttctcgtagtctgctttgctcagcgtcagggtgttg ctgaggctgtagg (SEQ ID NO: 23) |
| Ck3'-8 | ctagcactctccctgttgaagctctttgtgacgggcgagct caggccctg (SEQ ID NO: 24) |
| Ck5'-9 | gggatatcactgtggctgcaccatctgt (SEQ ID NO: 25) |
| Ck3'-16 | ggtctagactagcactctccctgttgaa (SEQ ID NO: 26) |

EXAMPLE 5

Example 5 describes the construction of the expression plasmid for producing the heavy chain and light chain of chimeric monoclonal antibody.

Plasmid 09EV030415-3-pcDNAMHH:

The expression plasmid, 09EV030415-3-pcDNAMHH, containing the full-length heavy chain cDNA of chimeric monoclonal antibody was produced by PCR method and cloned into the expression vector (pcDNA3.1(+)). In brief, for production of murine variable region cDNA fragment, the PCR was performed in a volume of 50 ul reaction mixture containing plasmid pTHV1 as DNA template, 100 ng of each forward primer(MOUHV5-5':5'-ggaagcttccaccatgaaggtgtg-gttaaac-3') (SEQ ID NO:27 and reverse primer (MUVHC1-3': 5'-tgggcccttggtggaggctgaggagactgtgag-3') (SEQ ID NO:28), 10 ul of 10× Pfu enzyme buffer, 0.2 mM dNTP, 5 U of Pfu DNA polymerase. PCR was carried out for 30 cycles in a thermal controller with 50 sec denaturing (95° C.), 50 sec annealing (55° C.), 1 min extension (72° C.), and a final extension of 10 min. The size of the PCR products was verified by 1% TAE agarose gel stained with ethidium bromide. The PCR product (DNA fragment Mv) was purified and used to further PCR.

For producing the human IgG1 constant region cDNA, the 50 ul of PCR reaction mixture consisting of 1× PCR buffer, plasmid 09EV030303-5-pTHclgG1 as DNA template, 100 ng of each forward primer (HUIgGC7-5':5'-gcctccaccaagggc-ccatcggtcttccccctggcaccctcctccaag-3') (SEQ ID NO:29) and reverse primer (HUIgGC6-3':5'-ggggaattctcatttacccggaga-cagggagaggctcttctg-3') (SEQ ID NO:30), 0.2 mM dNTP, 5 U of Pfu DNA polymerase. PCR was carried out for 30 cycles in a thermal controller with 50 sec denaturing (95° C.), 50 sec annealing (55° C.), 1 min extension (72° C.), and a final extension of 10 min. The PCR product (DNA fragment Hc) was purified and used to further PCR.

For cloning of chimeric monoclonal antibody cDNA, DNA fragment Mv and Hc were fused by the PCR. Briefly, PCR was performed in a volume of 50 ul using 20 ng of fragments Mv and Hc as DNA template, 5 U of pfu DNA polymerase, 5 ul of 10× PCR buffer, 200 uM each dNTP, and 100 ng of MOUHV5-5' and HUIgGC6-3' primers. PCR was carried out for 30 cycles in a thermal controller with 50 sec denaturing (95° C.), 50 sec annealing (55° C.), 1 min extension(72° C.), and final extension for 10 min. The PCR product was purified and digested with the Hind III and EcoR I, then subcloned into the Hind III-EcoR I sites of pcDNA3.1 (+) by T4 DNA ligase reaction. The reaction mixture was transferred into *E. coli* (DH5 α) by electroporation for replicating and maintaining plasmid. The DNA was verified by DNA sequence analysis. The exact construct is 09EV030415-3-pcDNAMHH and the plasmid map is shown in FIG. 3(*a*).

Plasmid 09EV030415pSV2DMHL:

The expression plasmid, 09EV030415pSV2DMHL, containing the full-length light chain cDNA of chimeric monoclonal antibody was produced by PCR method and cloned into the expression vector. The murine variable cDNA fragment was produced in a PCR reaction mixture containing plasmid 09EV030318-3-pyVk-F as DNA template, 100 ng of each forward primer (ChiMOU1-5':5'-CCGGCTAGCCAC-CATGGTATCCGCAGCTCAG-3') and reverse primer (Chi-MOU2-3':5'-CCGTTTTATTTCCAGCTTGGTC-CCCCCTCC-3'), 10 ul of 10× Pfu enzyme buffer, 0.2 mM dNTP, 5 U of Pfu DNA polymerase. PCR was carried out for 30 cycles in a thermal controller (Stratagene) ROBOCY-CLER 96™ with 50 sec denaturing (95° C.), 50 sec annealing (55° C.), 1 min extension (72° C.), and a final extension of 10 min. The size of the PCR products was verified by 1% TAE agarose gel stained with ethidium bromide. The PCR product (DNA fragment M1) was purified and used to further PCR.

For producing the human constant cDNA, PCR was performed in a a volume of 50 ul using plasmid 09EV030115pcDNACk8 as DNA template, 5 U of pfu DNA polymerase, 5 ul of 10× PCR buffer, 200 uM each dNTP, and 100 ng of ChiMHU3-5': 5'CTGG°T°ACGGACTGTGGCTGCACCA-3' (SEQ ID NO:33) and ChiHU4-3':5'-CCGTCTAGACTAGCACTCTC-CCCTGTTGM-3' (SEQ ID NO:34) primers. PCR was carried out for 30 cycles in a thermal controller with 50 sec denaturing (95° C.), 50 sec annealing (55° C.), 1 min extension(72° C.), and final extension for 10 min. The size of the PCR product (DNA fragment H2) was verified by 1% TAE agarose gel and purified for further PCR.

For construction of plasmid 09EV030415pSV2DMHL, the full-length of light chain cDNA was produced in a PCR mixture containing DNA fragment M1 and H2 as DNA template, 100 ng of forward primer ChiMOU1-5' and reverse primer ChiHU4-3', 10 ul of 10× Pfu enzyme buffer, 0.2 mM dNTP, 5 U of Pfu DNA polymerase. PCR was carried out for 30 cycles in a thermal controller with 50 sec denaturing (95° C.), 50 sec annealing (55° C.), 1 min extension (72° C.), and a final extension of 10 min. The PCR product was purified and digested with the Nhe I and Xba I, then subcloned into the Nhe I-Xba I sites of pSV2-dhfr-VEGF that was derived from pSV2-dhfr vector (ATCC37146) by T4 DNA ligase reaction. The reaction mixture was transferred into *E. coli* (DH5 α) by electroporation for replicating and maintaining plasmid. The DNA was verified by DNA sequence analysis. The plasmid map is shown in FIG. 3(b).

EXAMPLE 6

Example 6 discusses expression plasmid transfection and cell clone selection.

Forty (40) ug of maxiprep DNA from each expression vectors (09EV030415-3-pcDNAMHH and 09EV030415pSV2DMHL) were linearized by restriction enzyme Puv I digestion and $1.0 \times 10^7$ CHO-dhfr$^-$ cells were cotransfected by electroporation. Prior to transfect the cells were washed with two times ice-cold Berg Buffer and then resuspended in 0.5 ml of the same ice-cold buffer and placed in a 0.4-cm electrode gap electroporation cuvette (Bio-Rad) with the linearized vectors. The composition of the Berg Buffer is:

20 mM HEPES pH 7.05;
137 mM NaCl;
5 mM KCl;
0.7 mM Na2HPO4;
6 mM dextrose;
Sterilized by through 0.22 um filter.

For the electrical pulse, the GENE PULSER II™ (Bio-Rad) was set at a capacitance 975 uF and voltage 250 V. After two continuous pulses, cells were incubated on ice for 10 min then washed once with IMDM (GIBCO) supplemented with 0.1 mM hypoxanthine, 0.016 mM thymidine, and 10% FBS at a cell density of $10^5$ cells/ml.

After 48 hours recovery in complete medium (i.e., IMDM medium mentioned above), the transfected cells were plated into twenty 100-mm culture dishes in selection medium. The Selection Medium is: alpha MEM (GIBCO, Cat. #12000-022) supplemented with 10% dialysed FBS (Biological Industries, Cat. #04-011-1A) and 600 ug/ml G418 (CALBIOCHEM, Cat #345810).

Although the vectors were designed so that heavy and light chains contained different selectable markers (the neomycin and dhfr-phenotype), we found that the transfectants singlely selected usually synthesize both the transfected genes. Ten to fourteen days after the cells in selection medium, cell colonies can be seen by holding the dish above one's head at an angle to the overhead lights and looking for apaque patches, then using cloning cylinder to pick single stable colony. The picked cells were cultured in 24-well culture dish to expand the cell numbers.

EXAMPLE 7

Example 7 describes the amplification of stable transfectants.

Amplification is a long process. Before amplifying a stable transfectant, one should be sure that the gene of interest has indeed been integrated into the cell in a function form. You can examine the cellular DNA by Southern blotting, by examining the cellular RNA by Northern blotting, or by examining the cellular protein by Western blotting and/or ELISA.

The amplification process is illustrated as FIG. 4. Split the confluent dish of cells growing in the selection medium 1:6 into the same medium supplemented with 5 nM methotrexate (MTX) (Sigma, Cat. # M8407). As the cells grow to confluence, split them 1:6 again. The cells will grow slowly and take on a flat, spread-out morphology. This indicates that the cells are starved for DHFR.

Keep splitting the cells 1:6 into selection medium containing 5 nM methotrexate. When the rate of cells growth increases and when the cells begin to take on a more normal morphology, increase the degree of the split to 1:8, then 1:10, then 1:15. When the cells grow to confluence in 3 days form a 1:15 split and have recovered a normal morphology (polygonal-like shapes), the cells are ready for the next amplification step. Repeat the above process using the same selection medium supplemented with 20 nM methotrexate. Continue amplifying by increasing the concentration of methotrexate by 4-fold increments. The 5.12 uM MTX-amplified CHO clone #4 produced ~7 ug/ml of anti-EV71 chimeric antibody in the serum containing medium was selected for further purification development and characterization.

EXAMPLE 8

Example 8 describes the expression and purification of chimeric monoclonal antibody of EV71.

The MTX-amplified CHO clone #4 bearing the EV71 chimeric antibody genes (heavy and light chains) for protein expression was grown in Ex-cell™ 302 CHO-serum free medium (purchased from JRH, Cat#24326-10L) by spinner flask in a humidified incubator at 37° C. and 5% $CO_2$ for 7 days. Cells were removed by centrifugation (2000×g for 10 min). The 1.5 liter of clarified medium was concentrated by using a filter system (CROSS FLOWA UF™ (Sartorius)).

Figure 6:
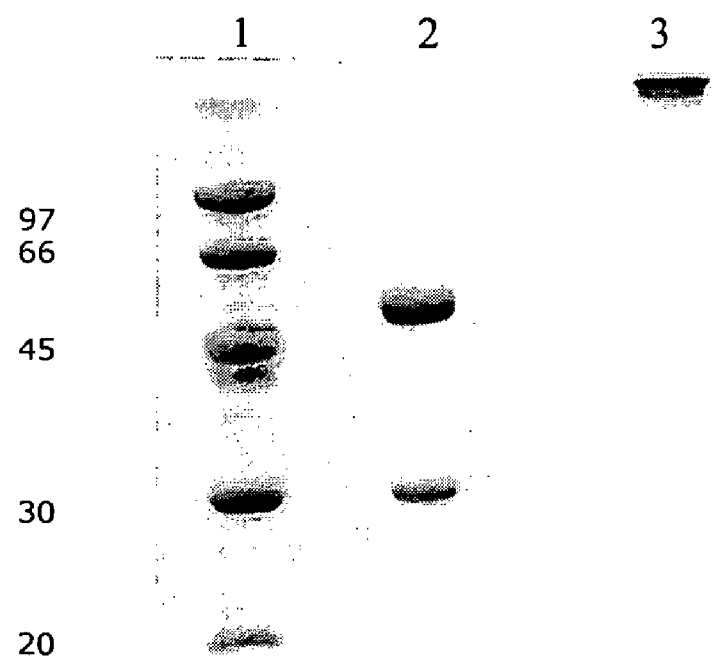
FIG. 6 illustrates 15% SDS-PAGE analysis of recombinant anti-EV71 chimeric antibody, specifically lane 1 relates to protein marker, lane 2 relates to protein sample resuspended in reducing buffer for PAGE, and lane 3 relates to protein sample resuspended in non-reducing buffer for PAGE.

The chimeric monoclonal antibody was purified in two chromatographic steps, rprotein A followed by gel filtration. After concentrated medium was loaded into rprotein A Sepharose column (5 ml, 10×60 mm), about 5 column volume of equilibration buffer (PBS, pH7.2) was used for washing unbound protein. The product was eluted by 5 column volume of elution buffer (0.1M sodium citrate, pH3.0)(FIG. 5(a)). The eluate was immediately neutralized with Tris buffer. After rProtein A purification, the protein eluate was loaded into gel filtration column (Superdex 200 prep, 450 ml, 26×90 mm). The equilibration and elution buffer are PBS buffer (pH7.2).The protein main peak (~150 kDa) was fractionately collected in 8 tubes (FIG. 5(b)). Fraction #3,4, and 5 were pooled as final purified product. The protein concentration of various fractions was determined by the UV spectrophotometric method and 15% SDS-PAGE analysis. The purity of the product is over 95%. The molecular weight of anti-EV71 chimeric antibody produced from CHO stable clone#4 is ~150 kDa expectedly and could be separated to heavy chain and light chain in reducing condition (FIG. 6).

EXAMPLE 9

Example 9 discusses the antigen binding ability in vitro by capture ELISA.

Figure 7:
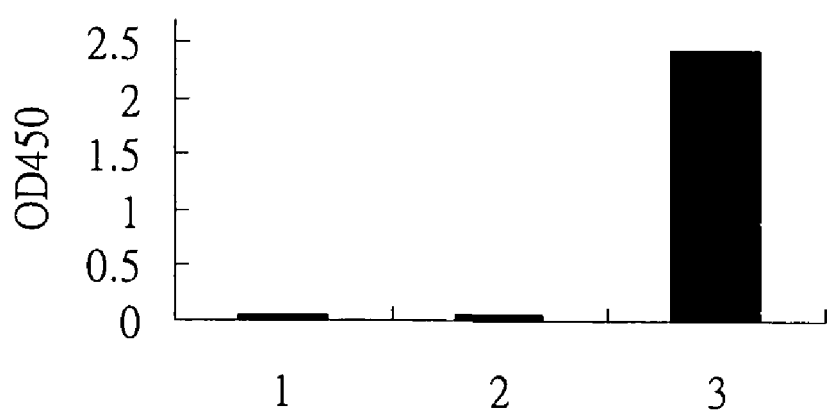
FIG. 7 shows the antigen binding ability by recombinant chimeric antibody, determined by the capture ELISA.

The 2 ug/ml of EV71 viral particle resuspended in 1× PBS buffer (pH7.4) was coated on the ELISA microtiter plate at 4° C. overnight. For ELISA, the diluted purified chimeric antibody was incubated with the pre-coated viral particles, then by using the biotinylated anti-human Fc antibody as the secondary antibody. The OD was determined at 450 nm following incubation of Steptavidin-HRP reagent (R&D System Inc., Cat#DY998) at room temperature for 20 min. The result is shown in FIG. 7. In FIG. 7 sample 1 is PBS buffer control, sample 2 is cell culture medium control, and sample 3: is purified chimeric antibody. The result indicates that the anti-EV71 chimeric antibody recognizes the whole viral particle specifically.

EXAMPLE 10

Example 10 describes in vitro viral neutralizing assay.

Purified chimeric antibody was subjected to the capability of neutralizing EV71 infection in vitro. To quantify the activity of viral naturalization, 50% of tissue culture infective does (TCID50) were determined with the method described by Hsiung GD (Husiung's Diagnostic Virology, ed4. New Haven, Yale University Press, 119-140; 1994). The Reed and Muench Formula was used.

Neutralizing antibodies were determined using a microassay with RD (rhabdomyosarcoma) cell line (ATCC CCL-136). Briefly, 50 μl of serial-diluted (two-fold dilution) sera were mixed with 50 μl of 100 $TCID_{50}$ EV71/4643 in a 96-well plate and RD cell suspension (final cell number is $8 \times 10^3$ cells) were added 2 h later. After incubation for 6 days at 37° C., neutralizing antibody titer was determined as the highest dilution of serum that inhibited virus induced cytopathic effect (CPE). The result is shown in Table 4. The result revealed that similar neutralization activities (neutralization titer dilution 1:8) were observed in both original murine and recombinant chimeric monoclonal antibodies. The humanized chimeric antibody could recognize the EV 71 viral particles specifically and neutralized the virus infectivity.

TABLE 4

The in vitro neutralization assay

| Ab | Dilution | 2 | 4 | 8 | 16 | 32 | 64 | 128 | 256 | 512 | 1024 | Cell control[c] |
|---|---|---|---|---|---|---|---|---|---|---|---|---|
| Purified monoclonal antibody produced from hybridoma 1G3 | | −[a] | − | − | +[b] | + | + | + | + | + | + | − | − |
| | | − | − | − | + | + | + | + | + | + | + | − | − |
| Purified recombinant chimeric monoclonal antibody from CHO clone#4[e] | | − | − | − | + | + | + | + | + | + | + | − | − |
| 1G3 supernatant[f] (unconcentrated) | | − | + | + | + | + | + | + | + | + | + | − | − |
| | | − | + | + | + | + | + | + | + | + | + | − | − |
| Hyperimmune[d] serum | | − | − | − | − | − | − | − | − | − | + | − | − |
| | | − | − | − | − | − | − | − | − | − | + | − | − |

[a]No CPE (cytopathic effect).
[b]CPE positive.
[c]Cells only for negative control.
[d]Mouse hyperimmune serum for positive control.
[e]Provided by ScinoPharm Biotech. Ltd.
[f]Un-concentrated wild type 1G3 culture supernatant.

The invention is not limited by the embodiments described above which are presented as examples only but can be modified in various ways within the scope of protection defined by the appended patent claims.

We claim:

1. A chimeric monoclonal antibody capable of binding enterovirus type 71 (EV71), wherein the chimeric monoclonal antibody comprises (i) a heavy chain variable region produced by mouse hybridoma cell line 1G3, and (ii) a light chain variable region produced by mouse hybridoma cell line 1G3.

2. The chimeric monoclonal antibody of claim 1 wherein the antibody comprises a constant region and a variable region, and the constant region is a human constant region.

3. The chimeric monoclonal antibody of claim 1 wherein the antibody is a humanized monoclonal antibody.

4. The chimeric monoclonal antibody of claim 1 wherein the chimeric monoclonal antibody has a purity of at least 95%.

5. The chimeric monoclonal antibody of claim 1, wherein the chimeric monoclonal antibody is capable of binding VP1 glycoprotein.

* * * * *

SEQUENCE LISTING

<160> NUMBER OF SEQ ID NOS: 34

<210> SEQ ID NO 1
<211> LENGTH: 405
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (1)..(405)

<400> SEQUENCE: 1

```
atg aag gtg tgg tta aac tgg cta ctt cct ttt att ctg tcg gta act    48
Met Lys Val Trp Leu Asn Trp Leu Leu Pro Phe Ile Leu Ser Val Thr
 1               5                  10                  15
```

```
tca ggg gtc tac tca gag gtt cag ctc cag cag tct ggg act gtg ctg      96
Ser Gly Val Tyr Ser Glu Val Gln Leu Gln Gln Ser Gly Thr Val Leu
         20                  25                  30 gca agg cct ggg gct tca gtg aag atg tcc tgc aag gcc tct ggt tac     144
Ala Arg Pro Gly Ala Ser Val Lys Met Ser Cys Lys Ala Ser Gly Tyr
     35                  40                  45 acc ttt acc acc tac tgg atg cac tgg ata aaa cag agg cct gga cag     192
Thr Phe Thr Thr Tyr Trp Met His Trp Ile Lys Gln Arg Pro Gly Gln
 50                  55                  60 ggt ctg gaa tgg att ggg act att ttt cct gga aat agt gat act agt     240
Gly Leu Glu Trp Ile Gly Thr Ile Phe Pro Gly Asn Ser Asp Thr Ser
 65                  70                  75                  80 tac aac cag aag tcc aag ggc aag gcc aaa ctg act gca gtc aca tcc     288
Tyr Asn Gln Lys Ser Lys Gly Lys Ala Lys Leu Thr Ala Val Thr Ser
             85                  90                  95 acc agc act gcc tac atg gag ctc agc agc ctg aca aat gag gac tct     336
Thr Ser Thr Ala Tyr Met Glu Leu Ser Ser Leu Thr Asn Glu Asp Ser
         100                 105                 110 gcg gtc tac tac tgt aca aga ttg agg gag ggc tac tgg ggc cac ggc     384
Ala Val Tyr Tyr Cys Thr Arg Leu Arg Glu Gly Tyr Trp Gly His Gly
     115                 120                 125 acc act ctc aca gtc tcc tca                                         405
Thr Thr Leu Thr Val Ser Ser
 130                 135

<210> SEQ ID NO 2
<211> LENGTH: 135
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 2

Met Lys Val Trp Leu Asn Trp Leu Leu Pro Phe Ile Leu Ser Val Thr
 1               5                  10                  15

Ser Gly Val Tyr Ser Glu Val Gln Leu Gln Gln Ser Gly Thr Val Leu
         20                  25                  30

Ala Arg Pro Gly Ala Ser Val Lys Met Ser Cys Lys Ala Ser Gly Tyr
     35                  40                  45

Thr Phe Thr Thr Tyr Trp Met His Trp Ile Lys Gln Arg Pro Gly Gln
 50                  55                  60

Gly Leu Glu Trp Ile Gly Thr Ile Phe Pro Gly Asn Ser Asp Thr Ser
 65                  70                  75                  80

Tyr Asn Gln Lys Ser Lys Gly Lys Ala Lys Leu Thr Ala Val Thr Ser
             85                  90                  95

Thr Ser Thr Ala Tyr Met Glu Leu Ser Ser Leu Thr Asn Glu Asp Ser
         100                 105                 110

Ala Val Tyr Tyr Cys Thr Arg Leu Arg Glu Gly Tyr Trp Gly His Gly
     115                 120                 125

Thr Thr Leu Thr Val Ser Ser
 130                 135

<210> SEQ ID NO 3
<211> LENGTH: 384
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
```

<221> NAME/KEY: CDS
<222> LOCATION: (1)..(384)

<400> SEQUENCE: 3

```
atg gta tcc gca gct cag ttc ctt ggt ctc ctg ttg ctc tgt ttt caa      48
Met Val Ser Ala Ala Gln Phe Leu Gly Leu Leu Leu Leu Cys Phe Gln
  1               5                  10                  15 ggt acc aga tgt gat atc caa atg aca cag cct aca tcc tcc ctg tct      96
Gly Thr Arg Cys Asp Ile Gln Met Thr Gln Pro Thr Ser Ser Leu Ser
             20                  25                  30 gcc tct ctg gga gac aga gtc acc atc agt tgc agg aca agt cag gac     144
Ala Ser Leu Gly Asp Arg Val Thr Ile Ser Cys Arg Thr Ser Gln Asp
         35                  40                  45 att agc aat tat tta aac tgg tat cag cag aaa cca gat gga act gtt     192
Ile Ser Asn Tyr Leu Asn Trp Tyr Gln Gln Lys Pro Asp Gly Thr Val
     50                  55                  60 aaa ctc ctg atc tac tac aca tca aaa tta cac tcc gga gtc cca tca     240
Lys Leu Leu Ile Tyr Tyr Thr Ser Lys Leu His Ser Gly Val Pro Ser
 65                  70                  75                  80 agg ttc agt ggc agt ggg tct gga aca gat tat tct ctc acc att gac     288
Arg Phe Ser Gly Ser Gly Ser Gly Thr Asp Tyr Ser Leu Thr Ile Asp
                 85                  90                  95 aac ctg gaa caa gag gat ttt gcc act tac ttt tgc caa cag ggt gac     336
Asn Leu Glu Gln Glu Asp Phe Ala Thr Tyr Phe Cys Gln Gln Gly Asp
            100                 105                 110 acg ctt ccg tac acg ttc gga ggg ggg acc aag ctg gaa ata aaa cgg     384
Thr Leu Pro Tyr Thr Phe Gly Gly Gly Thr Lys Leu Glu Ile Lys Arg
        115                 120                 125
```

<210> SEQ ID NO 4
<211> LENGTH: 128
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 4

```
Met Val Ser Ala Ala Gln Phe Leu Gly Leu Leu Leu Leu Cys Phe Gln
  1               5                  10                  15

Gly Thr Arg Cys Asp Ile Gln Met Thr Gln Pro Thr Ser Ser Leu Ser
             20                  25                  30

Ala Ser Leu Gly Asp Arg Val Thr Ile Ser Cys Arg Thr Ser Gln Asp
         35                  40                  45

Ile Ser Asn Tyr Leu Asn Trp Tyr Gln Gln Lys Pro Asp Gly Thr Val
     50                  55                  60

Lys Leu Leu Ile Tyr Tyr Thr Ser Lys Leu His Ser Gly Val Pro Ser
 65                  70                  75                  80

Arg Phe Ser Gly Ser Gly Ser Gly Thr Asp Tyr Ser Leu Thr Ile Asp
                 85                  90                  95

Asn Leu Glu Gln Glu Asp Phe Ala Thr Tyr Phe Cys Gln Gln Gly Asp
            100                 105                 110

Thr Leu Pro Tyr Thr Phe Gly Gly Gly Thr Lys Leu Glu Ile Lys Arg
        115                 120                 125
```

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic

```
                                          primer

<400> SEQUENCE: 5
gccggaattc tagaagcttt tttttttttt tttt                                    34

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aggtctagaa yctccacaca caggrrccag tggatagac                               39

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggggatatcc accatggrat gsagctgkgt matsctctt                               39

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggggatatcc accatgract tcgggytgag ctkggtttt                               39

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggggatatcc accatggctg tcttggggct gctcttct                                38

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)
<223> OTHER INFORMATION: a, c, g or t
<220> FEATURE:
<221> NAME/KEY: modified_base
<222> LOCATION: (34)
<223> OTHER INFORMATION: a, c, g or t

<400> SEQUENCE: 10
actagtcgac atgakgthcy cngctcagyt yctnrg                                  36
```

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
actagtcgac atggtrtccw casctcagtt ccttg                              35

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
actagtcgac atgtatatat gtttgttgtc tatttct                            37

<210> SEQ ID NO 13
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
actagtcgac atgaagttgc ctgttaggct gttggtgct                          39

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctcattcctg ttgaagctct tgac                                          24

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctggcaccct cctccaagag cacctctggg ggc                                33

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggtctagatc atttacccgg agacaggg                                      28

<210> SEQ ID NO 17
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
actgtggctg caccatctgt cttcatcttc ccgccatctg atgagcagtt gaaat     55

<210> SEQ ID NO 18
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gctgaataac ttctatccca gagaggccaa agtacagtgg aaggtggata acgcc     55

<210> SEQ ID NO 19
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tcccaggaga gtgtcacaga gcaggacagc aaggacagca cctacagcct cagca     55

<210> SEQ ID NO 20
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ctacgagaaa cacaaagtct acgcctgcga agtcacccat cagggcctga gctcg     55

<210> SEQ ID NO 21
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tagaagttat tcagcaggca cacaacagag gcagttccag atttcaactg ctcat     55

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tctgtgacac tctcctggga gttacccgat tggagggcgt tatccacctt     50

<210> SEQ ID NO 23

<211> LENGTH: 55
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
ttgtgtttct cgtagtctgc tttgctcagc gtcagggtgt tgctgaggct gtagg    55

<210> SEQ ID NO 24
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 24
ctagcactct ccctgttga agctctttgt gacgggcgag ctcaggccct g    51

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
gggatatcac tgtggctgca ccatctgt    28

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26
ggtctagact agcactctcc cctgttgaa    29

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
gggaagcttc caccatgaag gtgtggttaa ac    32

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
tgggcccttg gtggaggctg aggagactgt gag    33

<210> SEQ ID NO 29
<211> LENGTH: 48

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcctccacca agggcccatc ggtcttcccc ctggcaccct cctccaag                48

<210> SEQ ID NO 30
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggggaattct catttacccg gagacaggga gaggctcttc tg                      42

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccggctagcc accatggtat ccgcagctca g                                  31

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ccgttttatt tccagcttgg tcccccctcc                                    30

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ctggtacgga ctgtggctgc acca                                          24

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccgtctagac tagcactctc ccctgttgaa                                    30
```